United States Patent
Giordano et al.

(10) Patent No.: US 7,648,831 B2
(45) Date of Patent: Jan. 19, 2010

(54) PROCESS FOR MANUFACTURING AN INSOLUBLE BIOCATALYST

(75) Inventors: Roberto de Campos Giordano, São Carlos (BR); Raquel de Lima Camargo Giordano, São Carlos (BR); Andrea Lopes de Oliveira Ferreira, São Carlos (BR)

(73) Assignees: Fundacao Universidade Federal de Sao Carlos, Sao Carlos (BR); Fundacao de Amparo a Pesquisa do Estado de Sao Paulo, Sao Paulo (BR)

( * ) Notice: Subject to any disclaimer, the term of this patent is extended or adjusted under 35 U.S.C. 154(b) by 563 days.

(21) Appl. No.: 10/536,426

(22) PCT Filed: Nov. 24, 2003

(86) PCT No.: PCT/BR03/00173

§ 371 (c)(1),
(2), (4) Date: Oct. 31, 2005

(87) PCT Pub. No.: WO2004/050822

PCT Pub. Date: Jun. 17, 2004

(65) Prior Publication Data

US 2006/0127971 A1    Jun. 15, 2006

(30) Foreign Application Priority Data

Nov. 29, 2002 (BR) ................... 0205242

(51) Int. Cl.
| | |
|---|---|
| C12N 11/02 | (2006.01) |
| C12P 37/00 | (2006.01) |
| C12P 35/00 | (2006.01) |
| C12N 11/10 | (2006.01) |
| C12N 11/08 | (2006.01) |
| C12N 11/04 | (2006.01) |
| C12M 1/00 | (2006.01) |

(52) U.S. Cl. .......................... 435/177; 435/43; 435/47; 435/178; 435/180; 435/182; 435/289.1

(58) Field of Classification Search ........................ None
See application file for complete search history.

(56) References Cited

U.S. PATENT DOCUMENTS

| | | | | |
|---|---|---|---|---|
| 3,791,927 | A | * | 2/1974 | Forgione et al. ............ 435/182 |
| 4,138,292 | A | * | 2/1979 | Chibata et al. .............. 435/178 |
| 4,391,909 | A | * | 7/1983 | Lim ............................ 435/1.1 |
| 4,525,457 | A | | 6/1985 | Sakata et al. |
| 4,975,375 | A | | 12/1990 | Haruta et al. |
| 5,268,271 | A | * | 12/1993 | Guisan Seijas et al. ......... 435/43 |
| 5,286,495 | A | * | 2/1994 | Batich et al. ................. 424/490 |

FOREIGN PATENT DOCUMENTS

SU    785356 B    10/1980

OTHER PUBLICATIONS

N. Karpel Vel Leitner, et al, "A new photochemical reactor design for the treatment of absorbing solutions", Water Science and Technology, vol. 35, No. 4, pp. 215-222 © IWA Publishing 1997.
E.L. Koschmieder, "Bénard Cells and Taylor Vortices", Cambridge University Press 1993.
Christine M.V. Moore, "Characterization of A Taylor-Couette Vortex Flow Reactor", Massachusetts Institute of Technology, Sep. 1994.
Taylor, G.I., "Stability of A Viscous Liquid Contained Between Two Rotating Cylinders", Philosophical Transactions of the Royal Society, A,. vol. CCXXIII (1923), pp. 289-343.
Raquel L.C. Giordano, et al. "Performance Of A Continuous Taylor-Couette-Poiseuille Vortex Flow Enzymic Reactor With Suspended Particles", Process Biochemistry 35 (2000) 1093-1101.
R.L.C. Giordano, et al. "Analysis Of A Taylor-Poiseuille Vortex Flow Reactor-II: Reactor modeling and Performance Assessment Using Glucose-Fructose Isomerization as Test Reaction", Chemical Engineering Science 55 (2000) 3611-3626.
Jeffrey G. Sczechowski, et al. "A Taylor Vortex Reactor For Heterogeneous Photocatalysis", Chemical Engineering Science, 50, 3163-3173, 1995.

(Continued)

*Primary Examiner*—David M Naff
(74) *Attorney, Agent, or Firm*—Sughrue Mion, PLLC

(57) ABSTRACT

The purpose of the present invention is to provide a process for protection of enzymatic biocatalysts, constituted by a primary support, wrapped by a secondary matrix. More particularly, the invention is embodied as a bioreactor with a configuration that preserves the physical integrity and catalytic activity of the biocatalyst after long runs, and at the same time allows an easy separation of the protected biocatalyst from the solid, precipitated during the reaction course. Still more particularly, the invention refers to the use of the bioreactor herein described for the enzymatic synthesis of β-lactam antibiotics, including the insoluble enzymatic catalysts, which have a primary matrix for immobilization involved by a secondary matrix, which is able to preserve 100% of the catalyst physical integrity and approximately 100% of its catalytic activity.

8 Claims, 4 Drawing Sheets

OTHER PUBLICATIONS

Kunio Kataoka, et al., "Emulsion Polymerization of Styrene In A Continuous Taylor Vortex Flow Reactor", Chemical Engineering Science, vol. 50, No. 9, pp. 1409-1416, 1995.

G.A. Ameer, et al. "Investigation of a Whole Blood Fluidized Bed Taylor-Couette Flow Device for Enzymatic Heparin Neutralization", Biotechnology and Bioengineering, vol. 62, No. 5, pp. 602-608, Mar. 5, 1999.

Shimon Cohen, et al. "Analysis of a Rotating Annular Reactor In The Vortex Flow Regime", Chemical Engineering Science, vol. 46, No. 1, pp. 123-134, 1991.

K. Kataoka, et al., "Heat/Mass Transfer in Taylor Vortex Flow with Constant Axial Flow Rates", Int. J. Heat Mass Transfer. vol. 20. pp. 57-63. Pergamon Press 1977.

K. Kataoka, et al., Ideal plug-flow properties of Taylor vortex flow, Journal of Chemical Engineering Japan, vol. 8, pp. 472-476, 1977.

* cited by examiner

PROCESS FOR MANUFACTURING AN INSOLUBLE BIOCATALYST

FIELD OF THE INVENTION

The present invention reports a process for preparation of biocatalysts, made of an activated primary support to which enzymes are linked. The primary support, on its turn, is wrapped by a secondary matrix, which will provide mechanical protection and increase the particle size, making especially easier the separation of reaction products that crystallize during the process. This invention also refers to a reactor that promotes an efficient stirring, but without damaging the biocatalyst, using Taylor-Couette vortices and/or the injection of an inert gas.

BACKGROUND OF THE INVENTION

The huge worldwide competition in the biotechnology process industry puts forth several challenges. One of them is related to the ever-growing demands of governmental agencies that control environmental impacts. Thus, the search for new biochemical processes that are sustainable and, at the same time, economically competitive is a major driving force for this industry.

In this context, the use of enzymes in industry is increasingly intense. Enzymatic catalysis presents advantages when compared to classical processes:
  (i) reactions occur at room temperature and pressure;
  (ii) a specific reaction (reaction specificity) takes place on a particular site (site specificity). Therefore, the desired product may be obtained with high yields;
  (iii) since substrate specificity is high, only the desired compound is selectively reacted, even if there are other species present in the same environment.

However, enzymatic biocatalysts present drawbacks, namely:
  (i) if free enzyme(s) is(are) employed, its(their) re-use in successive batches, or their recycle in continuous reactors, is not economical, because they are soluble in water and present in low concentration;
  (ii) on the other side, if the enzyme(s) is (are) immobilized on insoluble supports, making possible the use in long journeys (repeated batches or continuous processes), the support matrices have, generally speaking, radii of the order of microns, to reduce pore diffusion effects. These biocatalysts (here understood as the support-enzyme assemble) have, in many instances, low shear stress resistance;
  (iii) such low-dimension biocatalysts are difficult to separate from precipitated products, whenever they are present in the process.

Additionally, enzyme activity may be reduced, sometimes irreversibly, by heat, by organic solvents, by acids or basis, or even by the reaction products. The proper biocatalyst (enzyme-support) engineering, however, may provide important gains in the catalyst life.

Research on immobilized biocatalysts has been performed since middle-50's. Presently, the following methods may be used for enzyme immobilization: (i) covalent binding, adsorption or ionic linking to the support; (ii) cross-linking, when enzyme molecules are interlinked by poly-functional reactants, and become insoluble; (iii) encapsulation, for instance in polymeric gel, microcapsules or lipid liquid membranes and (d) combinations of the previous methods.

Among these methods, gel encapsulation is more common, applied in the immobilization of several biocatalysts.

U.S. Pat. No. 4,975,375 describes a method for preparing a biocatalyst consisting of the following steps: (i) reducing the temperature of a reticulated polymeric gel, which has a specific phase transition temperature, and is able to reversibly expand or contract, expanding at temperatures lower than its phase transition's; (ii) adding the gel in the referred expanded state to a liquid medium with the enzyme, allowing the enzyme to migrate into it and (iii) heating at least a portion of the referred gel up to or above its transition temperature, what will cause its shrinking and, consequently, the entrapping of the enzyme.

Nevertheless, it should be pointed out that the classical methods have drawbacks, such as: (i) reducing enzyme activity after immobilization; (ii) lack of stability during the immobilization, making at least part of the molecules denature or change their conformation still outside the support; (iii) difficult reactivation of the catalyst; (iv) additional complications related to the immobilization reactions, which may be difficult to control or demand toxic reactants, hard to handle and (v) difficulties for the correct spatial orientation and precise positioning of the enzyme on the sites of interest of the support.

The association of a new method for enzyme immobilization with new configurations of integrate bioreactors is essential to make enzymatic processes feasible, complying with the reduction of environmental impacts while, at the same time, allowing a high process performance.

Bioreactors should preferably integrate, in the same equipment, the desired biochemical reaction, and stages of separation and purification of the desired product, such as its crystallization.

In the case of the production of semi-synthetic β-lactam antibiotics, one of the greatest drawbacks of the enzymatic route is its low selectivity, due to the competitive hydrolysis of the precursors (esters or amides) that would react with the β-lactam nuclei, and to the hydrolysis of the antibiotic itself. The same enzyme that promotes the synthesis catalyzes both undesired reactions.

The first semi-synthetic β-lactam antibiotic, derived after the substitution of the side-chain of penicillin G, was ampicillin (patented by Beecham, in 1961), followed by amoxicillin (Beecham patent, 1972) and by the semi-synthetic cephalexins (cephalexin, Lilly, 1970, cefazolin, Fujisawa, 1974, cephadroxil, BMS, 1977, among others). The evolution of the world market for these drugs was impressive ever since, from 1,000 ton/year in 1970 to 45,000 ton/year in 2000 (Moody H, Hogenboom A, Lange B, Heemskerk D, Dooren T V, Boesten W, Roos E. Enzymatic Production of Cephadroxyl. Oral communication and *Abstract Book of the 10th European Congress on Biotechnology*, CAT 12, Madrid, Spain, 8-11 Jul. 2001). These processes use chemical routes for the synthesis of the side-chains and for the condensation of the antibiotic, linking those chains to the proper β-lactam nucli (6-APA, nowadays obtained enzymatically from penicillin G, 7-ACA from cephalosporin C, and 7-ADCA, produced after the expansion, also via chemical route, of the thiazolidine ring of 6-APA). All these conventional processes are consolidated, but research is intense in this field, both in industry and academia, to establish an efficient enzymatic route.

To enhance the reaction selectivity, integrated reactors should be applied, with a biocatalyst constituted by the immobilized enzyme. In these reactors, antibiotic concentrations outrange their solubility limits in the process conditions. In this way, the desired product (in this case, the antibiotic) will precipitate before being attacked by the enzyme.

In conventional reactors, this process presents a series of drawbacks. In a well-mixed reactor, stirring will be too aggressive for the fragile particles of biocatalyst. Fluidized-bed reactors will demand high recycle flows, to sustain fluidization. Fixed-bed reactors may have serious mass transfer restrictions in the extra-particle film, decreasing the apparent reaction rates and, therefore, process productivity.

It is necessary, thus, to develop processes to manufacture immobilized enzymes, associated with integrated bioreactors that overcome the mentioned difficulties.

SUMMARY OF THE INVENTION

The purpose of the present invention is to provide a process for protection of enzymatic biocatalysts, constituted by a primary support, wrapped by a secondary matrix.

The present invention is put forth as a system for protection of enzymatic biocatalysts with radii between 1 and 4 mm.

More particularly, the invention is embodied as a bioreactor with a configuration that preserves the physical integrity and catalytic activity of the biocatalyst after long runs, and at the same time allows an easy separation of the protected biocatalyst from the solid, precipitated during the reaction course.

Still more particularly, the invention refers to the use of the bioreactor herein described for the enzymatic synthesis of β-lactam antibiotics, including the insoluble enzymatic catalysts, which have a primary matrix for immobilization involved by a secondary matrix, which is able to preserve 100% of the catalyst physical integrity and approximately 100% of its catalytic activity.

DETAILED DESCRIPTION OF THE INVENTION

Figure 1:
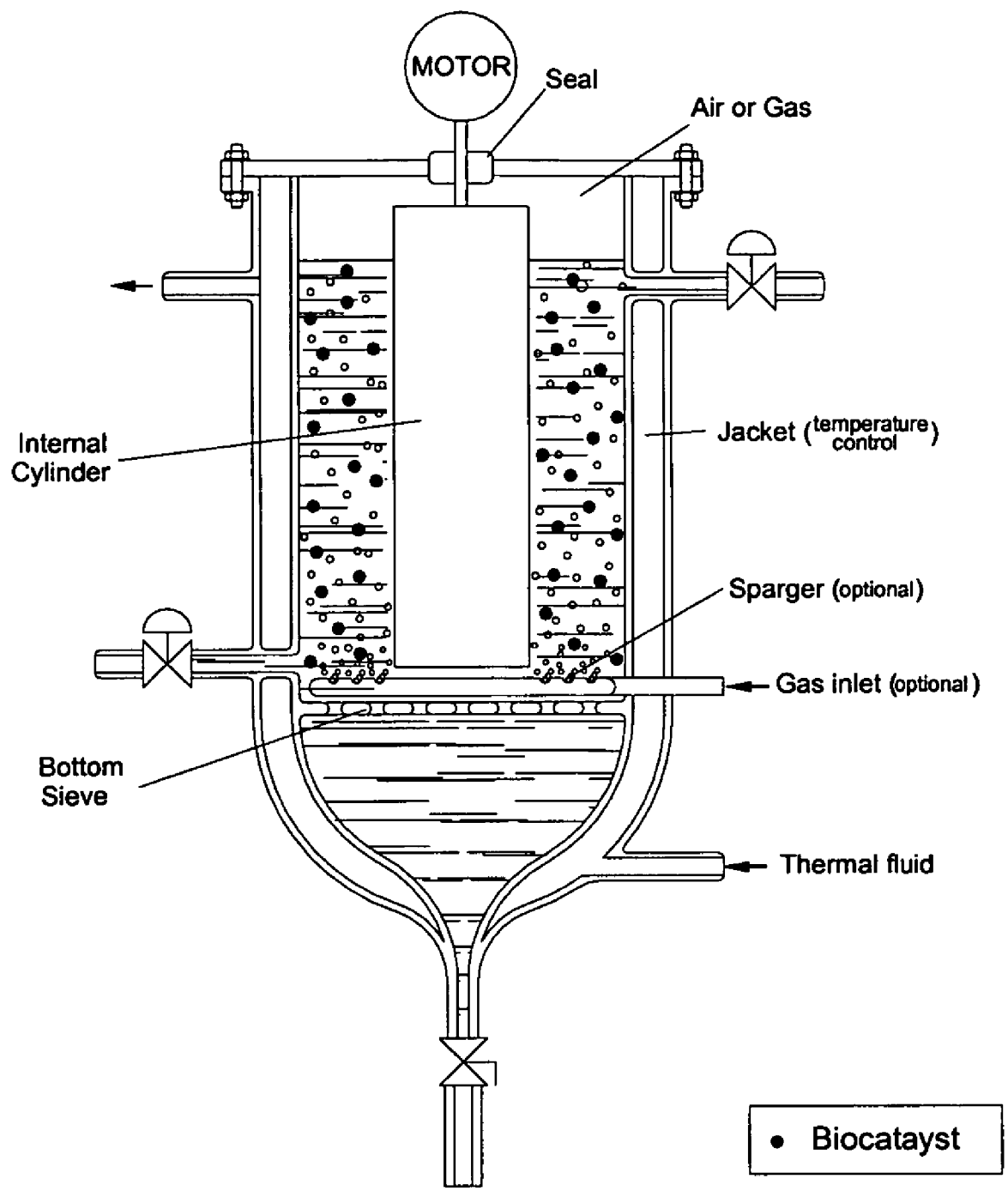
FIG. 1: Shows a scheme of the vortex flow reactor.

The invention herein described aims at defining a new procedure to encapsulate the active biocatalyst, such that its integrity is preserved after long journeys, and at the same time it describes a reactor configuration that allows a gentle (preserving the biocatalyst particles) and efficient stirring (homogenizing the particles' suspension and avoiding extra-particle mass transfer resistances).

One alternative to solve the previously mentioned difficulties is using a Taylor-Couette vortex flow reactor, which presents toroidal vortices in the gap between two cylinders, when the inner one rotates above a critical speed. This flow pattern presents some advantages. The reactor flow regime may be changed, between an almost plug-flow (for continuous reactors) and a perfectly mixed reactor, without changing residence times. Stirring gentle, although efficient, making it feasible for applications where low shear stresses are demanded (such as in the case of an enzyme support made of silica or gel). The inner cylinder rotation rate provides an additional degree of freedom for the operation of the reactor, allowing particle fluidization without changing axial flows.

Another important aspect of the integrate reactor is the protection of the enzyme carrier. When the desired product precipitates, the support must have a proper size, allowing its easy separation from the product crystals. At the same time, the support must be flexible, to bear the growth of these crystals without degradation along time. The proper combination of mechanical and physicochemical characteristics is a crucial step for the process.

Application of Taylor-Couette-Poiseuille flow in chemical and biochemical reactors has been reported ever since the work of Kataoka et al. (Kataoka K, Doi H E, Hongo T. Ideal plug-flow properties of Taylor vortex flow, *Journal of Chemical Engineering Japan*, 8, 472-476, 1977). Taylor vortices are a secondary flow pattern that appears in the annular gap between two cylinders, the inner rotary, and the outer generally stationary (Taylor G I. Stability of a Viscous Liquid Contained between Two Rotating Cylinders, *Philosophy Transactions of the Royal Society A*, 223, 289-343, 1923 e Koschmieder E L. Bénard cells and Taylor vortices. New York: Cambridge University Press, 1993). When an axial Poiseuille flow is superimposed to this pattern, one may operate the rector continuously. Above a critical rotation, the toroidal vortices appear, from the original Couette flow.

The use of bench-scale vortex flow reactors (VFRs) has been reported (Cohen S, Maron D M. Analysis of a Rotating Annular Reactor in the Vortex Flow Regime. *Chemical Engineering Science*, 46, 123-134, 1991; Kataoka K, Ohmura N, Kouzu M, Simamura Y E, Okubo M. Emulsion Polymerization of Styrene in a Continuous Taylor Vortex Flow Reactor. *Chemical Engineering Science*, 50, 1409-1416, 1995, Sczechowski J G, Koval C A E, Noble R D F. A Taylor Vortex Reactor for Heterogeneous Photocatalysis. *Chemical Engineering Science*, 50, 3163-3173, 1995 Leitner N K V, Le Bras E, Foulcault E, Bousgarbiès J-L. A New Photochemical Reactor Design for the Treatment of Absorbing Solutions. *Water Science and Technology*, 35, 215-222, 1997 Ameer G A, Harmon W, Sasisekharan R, Langer, R. Investigation of a whole blood fluidized bed Taylor-Couette flow device for enzymatic heparin neutralization. *Biotechnology and Bioengineering*, 62, 602-608, 1999). Giordano, R. L. C.; Giordano, R. C.; Prazeres, D. M. F.; Cooney, C. L.—Analysis of a Taylor-Poiseuille Flow Reactor-II: Reactor Modelling and Performance Assessment Using Glucose-Fructose Isomerization as Test Reaction". Chem. Eng. Science, V. 55, F18, p. 3611-26, 2000 e Giordano, R. L. C.; Giordano, R. C.; Cooney, C. L. "Performance of a Continuous Taylor-Couette-Poiseuille Vortex Flow Enzymatic Reactor with Suspended Particles"—Process Biochemistry, v. 35, F10, p. 1093-1011, 2000).

Nevertheless, industrial application of VFRs is still not widespread.

One special feature of the VFR is an incentive for its use as a bioreactor: its high flexibility with respect to the flow regime. Changing the inner cylinder rotation, the same equipment spans all the range from a perfectly mixed to a plug flow reactor. This characteristic makes it especially useful in multipurpose plants.

When an heterogeneous system is focused (for instance, with enzymes immobilized on a gel matrix or tissue cells anchored on particles), the rotation of the inner cylinder is an additional operation variable that may facilitate particle fluidization (Moore CMV. Characterization of a Taylor-Couette Vortex-Flow Reactor, Ph. D. Thesis, Massachusetts Institute of Technology, Cambridge, EUA, 1994). On the other side, the low shear stress of the Taylor flow is particularly interesting for bioprocess applications.

The present invention uses gels of citric pectin, alginate, carrageenam, among others, to wrap another matrix, that can be agarose, chitosan, silica, a microorganism—inactivated or not—among others. For instance, spherical particles of pectin gel may be conformed, involving other, smaller, of agarose gel, which on its turn is activated in a way that a certain enzyme may be immobilized on it.

In this way, it is intended to protect the immobilization support. At the same time, particles with higher diameters are obtained, which:
(i) avoid intra-particle diffusion effects;
(ii) resist the shear stress caused by mechanical agitation;
(iii) preserve their integrity when precipitation of one or more products occurs, so allowing the integration of the reaction and separation (by crystallization) steps in the same equipment;
(iv) be of adequate size, making it easy to separate the crystals of product from the biocatalyst at the end of the run.

These particles, on their turn, will be kept in suspension inside the reactor through an adequate stirring system, such as Taylor-Couette vortices and/or injection of an inert gas at the bottom of the reactor. In this way, it is intended to:
(i) achieve homogeneous fluidization of the particles without exposing them to excessive shear stress, keeping their integrity for long periods of operation;
(ii) reduce diffusional delays in the extra-particle liquid film; and
(iii) allow a flexible operation of the reactor, which may be used in batch, semi-batch or continuous mode, according to the needs of the process.

The enzyme of interest is previously immobilized on an activated, insoluble support, allowing a covalent link of the reactive groups. Immobilization may occur, for instance, through the link of aldehyde groups, generated on the support after a previous activation, with amino groups of the enzyme; or of epoxy groups of the support with different reactive groups of the enzyme, such as amine, hydroxyl, carboxyl and thiol; or of cycle-iminocarbonate groups of the support (generated after activation with CNBr) with amino groups of the enzyme, among other possibilities for immobilization. Activated supports may be: controlled-porosity silica, activated with glycidoxyethyltrimetoxysilane or with glutaraldehyde; agarose gel activated with glyoxil or glutaraldehyde groups; chitosan gel activated with glutaraldehyde; epoxy supports, among others. The system (activated support-reacted-with-enzyme) will be called here primary matrix.

For instance, the primary matrix may be agarose gel, ranging between 6% and 10% (w/w), crosslinked, previously activated with glyoxil groups that promote multiple covalent links with amino groups of the lysine residues of the enzyme penicillin G acylase. Particle diameters may range between 60 μm e 300 μm. Enzymatic loads may range between 250 IU/(g of agarose gel) and 600 IU/(g of agarose gel), where 1 IU corresponds to the quantity of enzyme that hydrolyses 1 μmol of penicillin G by minute at pH 8 and 37° C.

According to the present invention the primary matrix, previously prepared, is wrapped by a second gel, such as citric pectin crosslinked with calcium, calcium alginate or other bivalent cation as zinc or magnesium, or transition metals as iron, among others (secondary matrix). A solution of pectin or sodium alginate in water (the ratio mass of polymer/total mass may vary, between 0.5 and 3% for alginate and 2-6% for pectin) is mixed to the primary matrix in different proportions, depending on the final enzymatic load that is sought. Typical values of this ratio are between 1:5 and 1:20 (mass of primary matrix/mass of secondary matrix). The resulting suspension is extruded with spherical shape, with aid of a peristaltic pump. Spheres diameter is a function of the extrusion flow, of the diameter of the outlet tube or needle used for dripping the suspension, and of the airflow, parallel to this tube or needle, which is used to accelerate the fall of the drop from the extruder tip. Typical diameters range between app. 0.5±0.1 mm and 2.0±0.1 mm. The drop of the suspension formed by the polymer solution and by the primary matrix is put into contact with a solution of a salt with a bivalent cation such as calcium, magnesium or zinc, or transition metals such as iron. The chains of polymer, for instance pectin or alginate, dissolved in water, are approximated through crosslinks with the cation, producing the water-insoluble gel. At first, only the external area of the sphere becomes rigid. The rate of the reaction that turns rigid the interior of the gel (cure) and the final number of crosslinks cation-polymer depend on the concentrations of cation and polymer, of the time of cure and of the reaction temperature. For instance, a solution 0.2 M of $CaCl_2$, with 2% (w/w) of alginate or 6% (w/w) of pectin, must be cured for at least 2 hours at room temperature. Keeping the pectin or alginate gel integrity in the enzymatic reactor demands the presence of the cation in the medium or, alternatively, the use of reactivation cicles between batches. In the following examples, the ratio of calcium is reset after 24-h runs. The biocatalyst is immersed in 0.2 M of $CaCl_2$ for 2 h, between two runs of the reactor. The final density of the biocatalyst may change considerably, depending on the primary matrix and on the ratio (enzymatic derivative/polymer solution). Particles more or less dense than the medium may be manufactured. In the following examples, the apparent density of the particles in water is 1.01 g/mL.

As to the reactor, they must provide adequate agitation: enough to homogenize the medium and eliminate or reduce extra-particle resistances to mass transfer. A scheme of the vortex flow reactor (VFR) is in FIG. 1. It may be operated continuously, in fed-batch or batch mode. For continuous operation, feeding is at the bottom and the outlet at the top of the reactor.

According to the present invention, the particles are not affected by shearing forces, for rotations of the inner cylinder between 200 rpm and 2000 rpm. An important feature is to maintain the internal cylinder in balance, in vertical position. A bearing at the bottom of the inner cylinder would demand a seal—in the internal cylinder, if the bottom of the reactor is immobile, or at the external wall, if a rotary bottom were used for the vessel. In any case, the rotation of the vortex close to the bottom end of the apparatus would drag the particles towards the seal, causing its mechanical grinding. Hence, this invention uses an internal cylinder that is kept in balance, supported only at its top extremity. To avoid the contact of particles with the upper seal, a small overhead space filled with air (or inert gas) is in the gap above the liquid, at the top of the reactor. Biocatalyst particles are retained in the gap between cylinders and the ratio of cylinders' radii is in the range 0.20-0.60 (app.). Other geometries may be used in place of the inner, rotary cylinder. For instance, conic sections or other revolution surfaces may improve crystal segregation in the integrate reactor (where the product precipitates), which will separate from the biocatalyst particles.

Injection of small flow of a gas (air, for instance) may be also used to help particles homogenization.

Different schemes may be used to separate crystals and catalyst. One may be draining the reactor through a sieve with large grid (0.2-1.0 mm, for instance). The biocatalyst described in this invention has diameter in the order of millimeters, while the solid precipitates with less than 100 μm. Clogging problems, typical in other configurations of integrate reactors, are therefore avoided. Another way to remove the precipitate is using its difference in size with respect to the catalyst to segregate the two kinds of solid, forcing an up-flow through the VFR with a slow rotation of the inner cylinder (or conic section, among other geometries). The reactor is washed with a supersaturated solution of the desired product—for instance, the antibiotic—and the crystals are collected at the top. A large-grid sieve may also be used at the top outlet of the reactor, to retain the biocatalyst while withdrawing the precipitated product. In this case, the operation of the reactor may be continuous.

The flexibility of this reactor can be explored in a number of applications. Depending on the density of the support used in the biocatalyst, on the size of the produced crystals, on the viscosity of the reaction medium, among other factors, the most adequate solution may be chosen. Several operational regimes may also be used, for different processes: batch, semi-continuous and continuous.

Figure 2:
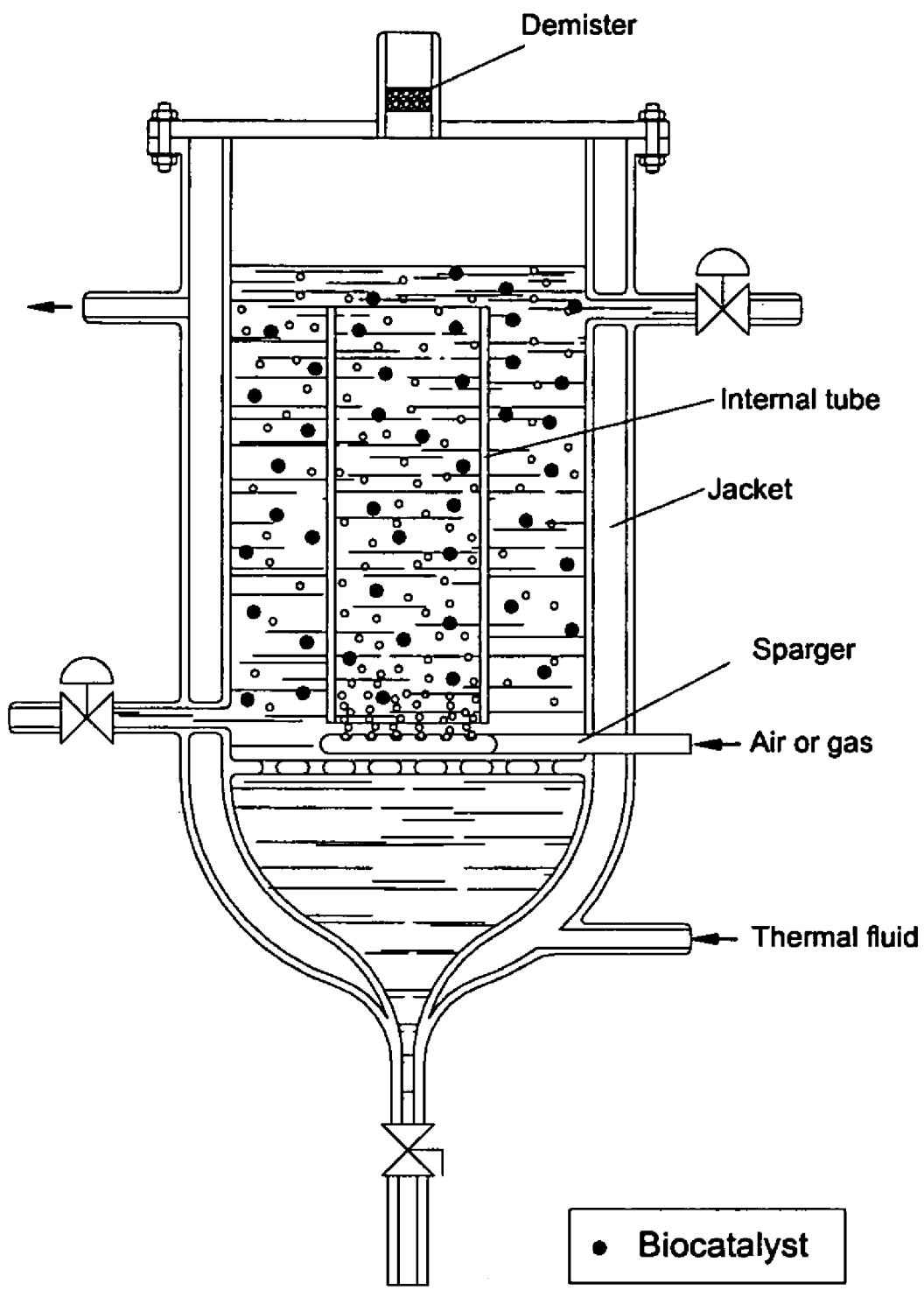
FIG. 2: Shows the scheme of an air-lift reactor.

Another option for the reactor described in this invention is using an air-lift configuration, see FIG. 2.

In this case, a sparger at the bottom of the reactor promotes mixing. An internal cylinder may be put in the apparatus, thus ordering particle movement (air-lift reactor). The biocatalyst described in this invention, with two support matrices and immobilized enzyme will reduce the possibility of inactivation caused by the gas hydrophobicity. The gas may be air, nitrogen, $CO_2$ or any other known by experts in the field, adequate to the specific process. In this case, the proper injection of gas will also promote the homogenization of the medium without affecting the previously described biocatalyst. The product, in solid phase, is collected at the bottom of the reactor, separated from the biocatalyst by a sieve equal to the one described for the VFR. In the case of continuous operation, a sieve at the reactor top outlet allows removing the crystals while the biocatalyst is retained.

The following examples illustrate the invention and represent preferred embodiments. Experts in the field will be able to carry out no more than routine experiments to use other materials, techniques or appropriate configurations.

EXAMPLE 1

Definitions And Analytical Methods

Support—primary matrix: Agarose 10% (w/w), crosslinked, Hispanagar S/A. (Spain).

Support—secondary matrix: Citric pectin with low metoxilation, type 8002, Braspectina do Brasil.

Enzyme: Penicillin G acylase (PGA) from *Escherichia coli* [EC 3.5.1.11], Antibióticos S/A, Leon, Spain.

Substrates: phenylglycine metyl ester PGME (Aldrich Chemical Co.); 6-aminopenicillanic acid, 6-APA (Winlab, obtained after the enzymatic hydrolysis of penicillin G), ampicillin (Winlab) and phenylglycine (Aldrich Chemical Co.).

PGA immobilization: procedures described in the patent ES 2.005.883-A6.

Enzymatic activity: 1 IU (international unity) of enzymatic activity is defined as the amount of enzyme that hydrolyses 1 µmol of penicillin G per minute at pH 8 and 37° C.

Analisys: Concentrations of PGME, 6-APA, ampicillin and PG using HPLC. Column Waters C18: Nova-Pak, 60 Å, diameter 4 µm, 3.9×150 mm. Mobile phase: 35% acetonitrile, 2‰ SDS (sodium dodecyl sulfate), 10 mM $H_3PO_4$, 5 mM $K_2H_2PO_4$, pH 4.6 and 25° C., 225 nm, flow 1 mL/min.

Synthesis experiments: 25° C., pH 6.5 controlled by automatic addition of NaOH. Jacketed glass vortex flow reactor, internal cylinder of stainless steel 316. Reaction volume, 50 mL. Reactor internal diameter, 36 mm. Rotary cylinder diameter, 10 mm (radius ratio 0.28). Volume of biocatalyst, 20 mL. Enzymatic load, 10 IU/(mL of reactor).

EXAMPLE 2

Figure 3:
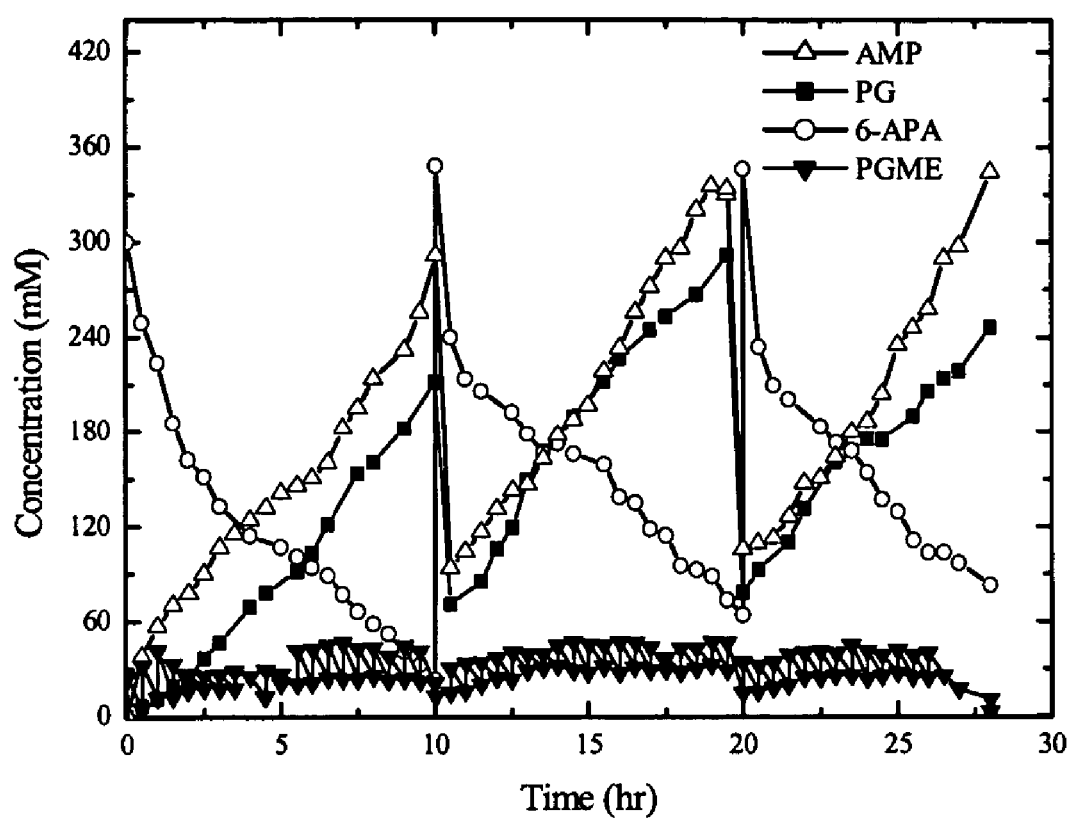
FIG. 3: Illustrates the synthesis of ampicillin (AMP) with crystallization of Penylglicine (PG) and AMP, 25° C., pH 6.5. Enzymatic load=10000 IU/L$_{reactor}$. Continuous feed of one substrate (PGME) during each run.

Vortex flow reactor, 25° C., pH 6.5, enzymatic load 10000 IU/$L_{reactor}$. Initial concentrations: 6-APA=300 mM; PGME=25 mM. Repeated fed batch operation, feeding PGME. Time span of each run=10 h. FIG. 3 shows typical results of three successive stages. Draining time is not shown.

In this example, specific productivity reached app. 4.5× $10^{-5}$ mmol/(IU.min), and absolute productivity de 0.45 mM/min. Selectivity at the end of each load was 3.6 mol antibiotic/(mol of PG). Instantaneous selectivity ranged from 3 and 6 during each stage of operation. Enzymatic activity and physical integrity of the biocatalyst remained unaltered.

EXAMPLE 3

Figure 4:
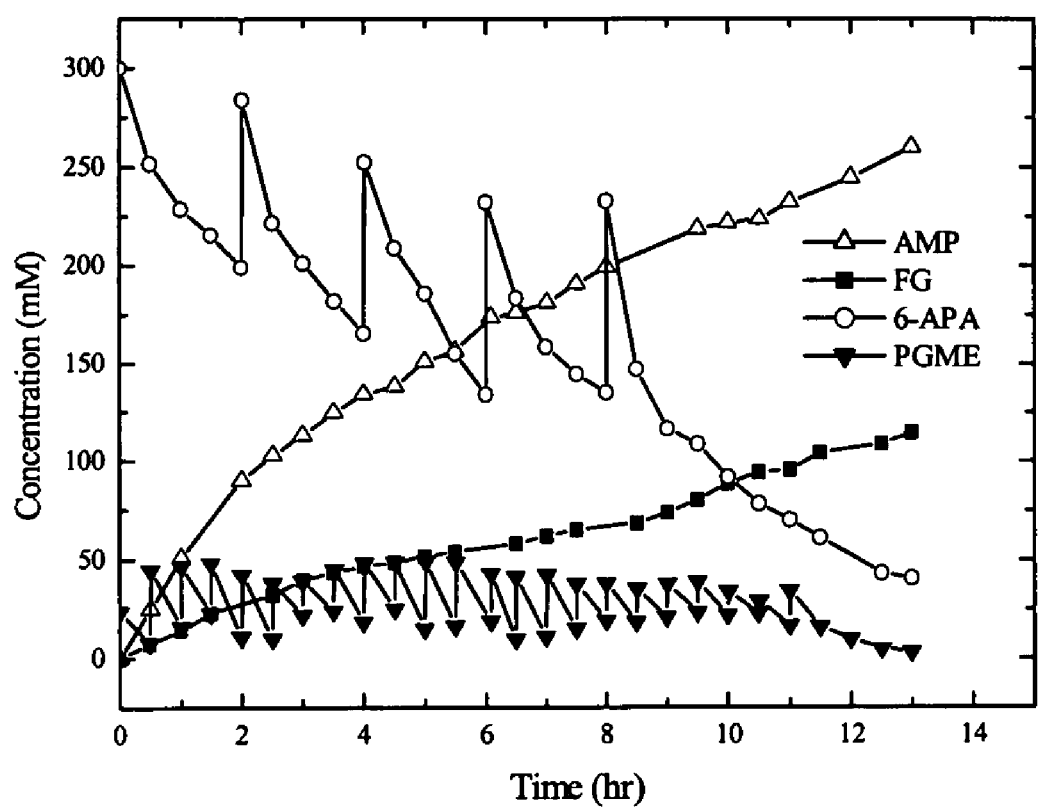
FIG. 4: Shows the synthesis of ampicillin with crystallization of PG and AMP, 25° C., pH 6.5. Enzymatic load=10000 IU/L$_{reactor}$. Continuous feed of two substrates (PGME and 6-APA) during each run.

Vortex flow reactor, 25° C., pH 6.5, enzymatic load 10000 IU/$L_{reactor}$. Initial concentrations: 6-APA=300 mM; PGME=25 mM. Repeated fed batch operation, feeding PGME and 6-APA. Time span of each run=10 h. FIG. 4 shows typical results of one stage.

In this example, specific productivity reached app. 3.5× $10^{-5}$ mmol/(IU.min), and absolute productivity of 0.44 mM/min. Selectivity at the end of each load was 2.4 mol antibiotic/(mol of PG). Instantaneous selectivity ranged from 2 and 6 during each stage of operation. Enzymatic activity and physical integrity of the biocatalyst remained unaltered.

The invention claimed is:

1. A process for manufacturing an insoluble biocatalyst, comprising the steps of:
    (1) immobilizing an enzyme to a support, wherein said support contains reactive groups and wherein said immobilization occurs by covalent bonding between said enzyme and said reactive groups; and
    (2) enveloping said support from step (1) with a matrix to form an insoluble biocatalyst, wherein said matrix is formed by cross-linking of polymers in a polymeric solution containing said support from step (1) such that the weight ratio between said support and said matrix of said biocatalyst is between 1:5 and 1:20, and the diameter of said insoluble biocatalyst is between 0.5±0.1 mm to 2.0±0.1 mm.

2. The process according to claim 1, wherein said polymer is selected from the group consisting of citric pectin, alginate and carrageenan.

3. The process according to claim 1, wherein said weight ratio is about 1:10.

4. The process according to claim 1, wherein said cross-linking occurs by contacting said polymeric solution with a salt solution containing at least one bivalent cation.

5. The process according to claim 4, wherein said bivalent cation is either a transition metal, or a metal selected from the group consisting of calcium, magnesium and zinc.

6. The process according to claim 4, wherein said salt solution is 0.2M $CaCl_2$.

7. A biocatalyst obtained according to the process of claim 1.

8. A biocatalyst obtained according to the process of claim 6.

* * * * *